United States Patent [19]

Noteisz et al.

[11] 4,184,040
[45] Jan. 15, 1980

[54] HYDROXYMETHYL-PYRIDINE ESTERS AND A PROCESS FOR THE PREPARATION THEREOF

[75] Inventors: Ferenc Noteisz; Mihály Bartók; Károly Felföldi, all of Szeged; Egon Kárpáti; László Szporny, both of Budapest, all of Hungary

[73] Assignee: Richter Gedeon Vegyeszeti Gyar Rt., Budapest, Hungary

[21] Appl. No.: 839,605

[22] Filed: Oct. 5, 1977

[30] Foreign Application Priority Data

Oct. 8, 1976 [HU] Hungary ............................... RI 598

[51] Int. Cl.² ............................................. C07D 213/55
[52] U.S. Cl. ....................................... 546/342; 424/263
[58] Field of Search ........ 260/295 R, 295 T, 295.5 T, 260/295.5 R; 424/263; 546/342

[56] References Cited
U.S. PATENT DOCUMENTS

| 3,100,775 | 8/1963 | Rorig | 260/295 R |
| 3,786,059 | 1/1974 | Walther et al. | 260/295 R |

OTHER PUBLICATIONS

Harry L. Yale, Journal of Medicinal and Pharmaceutical Chemistry, vol. 1, #2, 1959, pp. 121–133.

*Primary Examiner*—Richard Raymond
*Attorney, Agent, or Firm*—Karl F. Ross

[57] ABSTRACT

New hydroxymethyl-pyridine esters of the formula (I)

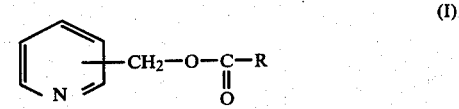

(I)

wherein R represents a 9-xanthenyl group or a phenyl group substituted by a halogen atom or a trifluoromethyl group or by an alkyl or alkoxy group, either having 1 to 4 carbon atoms, and pharmaceutically acceptable acid addition salts and quaternary salts thereof are prepared by acylating the corresponding hydroxymethyl pyridines with a carboxylic acid of the formula R—COOH, or with a reactive derivative thereof, and, if desired, converting the obtained product of the formula I into a pharmaceutically acceptable acid addition salt or quaternary salt thereof. The new compounds exert beneficial effects on functional disorders of the heart.

4 Claims, No Drawings

HYDROXYMETHYL-PYRIDINE ESTERS AND A PROCESS FOR THE PREPARATION THEREOF

The invention relates to novel compounds having antiarrhythmic activity. More particularly, the invention relates to the new hydroxymethyl pyridine esters of the formula (I)

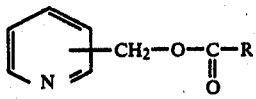
(I)

wherein R represents a 9-xanthenyl group or a phenyl group substituted by a halogen atom or a trifluoromethyl group or by an alkyl or alkoxy group, either having 1 to 4 carbon atoms, and to the pharmaceutically acceptable acid addition salts and quaternary salts thereof, as well as to a process for the preparation of the said compounds.

The new compounds of the formula (I) are esters of hydroxymethyl-pyridines formed with xanthene-9-carboxylic acid or with a monosubstituted benzoic acid and the pharmaceutically acceptable acid addition salts and quaternary salts of these esters.

The preparation of esters of hydroxymethyl pyridines formed with unsubstituted benzoic acid has been described in several papers [Arch. Pharm. 287, 505–514 (1954); J. Org. Chem. 27, 3858–3860] without mentioning any pharmacological properties of these compounds. Some nitrobenzoic acid esters of related structure have been prepared too, similarly without recognizing the pharmacological effects of the products [Annalen, 732, 1–6 (1970)]. Further known esters of hydroxymethyl pyridines are the trimethoxy benzoates having cholinergic [Pharmazie 13, 195–199 (1958)] and hypotensive [C.A. 53, 1326b] effects.

It has now been found that the hitherto unknown xanthene-9-carboxylic acid esters and monosubstituted benzoic acid esters of the formula I have valuable pharmacological properties of quite another type: they exert beneficial effects on functional disorders of the heart, as will be shown below.

The new compounds of the invention are prepared according to the invention by acylating a hydroxymethyl pyridine of the formula II

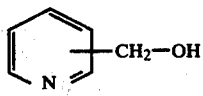
(II)

with a carboxylic acid of the formula R—COOH, wherein R has the same meaning as above, or with a reactive derivative thereof and, if desired, converting the obtained product of the formula I into a pharmaceutically acceptable acid addition salt or quaternary salt thereof.

All compounds of the formula I are new products. The starting compounds of the process described above are already known.

According to one method of carrying out the process of the invention, the starting hydroxymethyl pyridine is acylated with the corresponding free carboxylic acid. This acylation reaction is performed preferably in the presence of a carboxyl-activator and/or a water-binding agent. Mainly halogenated phenols or nitro-halogen-phenols, preferably pentachlorophenol and/or N,N'-dicyclohexyl-carbodiimide are used as carboxyl-activating agents.

According to a preferred embodiment of the process of the invention, the hydroxymethyl-pyridines are acylated with an acid halide of the corresponding carboxylic acid, preferably with the acid chloride thereof. The acylation reaction is preferably performed in the presence of an acid-binding agent. E.g. alkali metal carbonates may be used as acid-binding agents, but the preferred acid-binding agent is an excess of the hydroxymethyl-pyridine starting compound. In this case two moles of the hydroxymethyl-pyridine is reacted with one mole of the acid halide used as acylating agent.

The reaction may be carried out in an inert anhydrous organic solvent, e.g. in a hydrocarbon of the benzene series such as benzene, toluene or xylene, in a chlorinated hydrocarbon such as chloroform or carbon tetrachloride, or in an aliphatic ketone such as acetone, methyl-isobutyl ketone.

The reaction temperature may vary within wide limits, but preferably the acylating agent is added with cooling, at 0° to 30° C. to the solution of the hydroxymethyl-pyridine and then the reaction mixture is kept at elevated temperature, suitably at the boiling temperature of the reaction mixture. The precipitated acid addition salt of the hydroxymethyl-pyridine is then filtered off and the desired product is recovered from the filtrate by extraction and/or evaporation.

According to a further preferred embodiment of the process of the invention, the hydroxymethyl-pyridine starting compound is acylated with an ester of the carboxylic acid R-COOH (i.e. a reactive derivative of the carboxylic acid) formed with an aliphatic alcohol having 1 to 5 carbon atoms, preferably with the methyl or ethyl ester thereof. The acylation reaction is carried out preferably in the presence of a catalytic amount of an alkali alkoxide, preferably sodium or potassium methoxide or ethoxide. The acylating ester is added in a twofold or threefold molar excess to the hydroxymethyl-pyridine. The reaction can be carried out in the presence or absence of one of the solvents mentioned above.

The reaction temperature can vary within wide limits, e.g. between 35° and 130° C. Preferably the reaction is carried out at the reflux temperature and the aliphatic alcohol having 1 to 5 carbon atoms, which is liberated in the course of the reaction, may be removed by distillation. After cooling the reaction mixture and dissolving the residue in one of the solvents mentioned above, the desired product can be recovered by extraction.

The obtained product of formula I can be isolated and purified by per se known methods, or, if desired, converted into an acid addition salt or quaternary salt without previous separation from the reaction mixture.

The acid addition salts may be prepared by reacting the bases of formula I with pharmaceutically acceptable inorganic or organic acids, e.g. with hydrochloric, hydrobromic, hydroiodic, sulfuric or phosphoric acid or with acetic, propionic, butyric, maleic, fumaric, citric, malic, tartaric acid and the like.

The quaternary salts may be formed first by with alkyl halides having 1 to 5 carbon atoms, but also other compounds suitable for forming quaternary salts may be used for this purpose, provided that they are physiologically harmless and pharmacologically acceptable.

The preparation of the quaternary salts may be performed in known manner, e.g. by dissolving the base of the formula (I) in an organic solvent, preferably in an aliphatic ketone, e.g. in acetone and then adding the quaternizing agent to the solution of the base. The reaction mixture can be heated slightly or boiled and then allowed to stand under cooling. The precipitated crystals are separated by filtration, washed and dried; they may be also recrystallized, if necessary.

The compounds of the formula (I) inhibit disorders of the heart-rhythm. The inhibiting effect exerts itself in the rising of the threshold of the electric fibrillation of the heart. The pharmacologic tests were made on narcotized cats [cf. L. Szekeres and J. Papp: British J. Pharmacol. 17, 167 (1961)] and the activity of the tested compounds was characterized by the percentage of the increase of the fibrillation threshold limit, compared to the value before the administration of the compound. Six parallel tests were made for each dosage of each compound, the average values of the obtained results are shown below in Table 1. The values obtained by the same method with quinidine (an antiarrhythmic agent used successfully in therapy) are given in the Table for comparison.

Table 1

| | Percentage increase of the fibrillation threshold in relation to the value before the administration of the compound | | |
|---|---|---|---|
| | | Doses | |
| Compound | 2.0 mg/kg | 1.0 mg/kg | 0.5 mg/kg |
| 2204 | 27.4 | 15.2 | — |
| 2206 | 12.6 | — | — |
| 2208 | 12.9 | — | — |
| 2209 | 14.2 | — | — |
| 2213 | 18.6 | — | — |
| 2214 | 14.1 | — | — |
| 2215 | — | 14.2 | — |
| 2216 | — | 34.8 | 17.5 |
| 2217 | — | 32.1 | 14.8 |
| 2218 | — | 12.7 | — |
| 2221 | — | 27.6 | 13.9 |
| 2222 | — | 13.5 | — |
| quinidine | 34.5 | 20.6 | — |

It can be seen from the data of Table 1 that the antiarrhythmic activity of numerous new compounds is of the same or even higher level than the activity of quinidine. Thus especially the compounds No. 2216, 2217, 2221 and 2204 have shown high activities. The activity of the compound No. 2216 is nearly twice greater than that of quinidine.

The reference numbers given in Table 1 refer to the following new compounds of the invention:
2204: 4-(xanthene-9-carbonyloxymethyl)-pyridine hydrochloride
2206: 3-(xanthene-9-carbonyloxymethyl)-pyridine methyliodide
2208: 4-[(4-methoxybenzoyl)-oxymethyl]-pyridine hydrochloride
2209: 4-[(4-fluorobenzoyl)-oxymethyl]-pyridine hydrochloride
2213: 3-[(3-methoxybenzoyl)-oxymethyl]-pyridine hydrochloride
2214: 3-[(4-fluorobenzoyl)-oxymethyl]-pyridine hydrochloride
2215: 3-[(4-methoxybenzoyl)-oxymethyl]-pyridine methyliodide
2216: 3-[(3-trifluoromethylbenzoyl)-oxymethyl]-pyridine methyliodide
2217: 3-[(4-fluorobenzoyl)-oxymethyl]-pyridine methyliodide
2218: 2-[(2-methoxybenzoyl)-oxymethyl]-pyridine methyliodide
2221: 2-[(2-chlorobenzoyl)-oxymethyl]-pyridine methyliodide
2222: 2-[(4-fluorobenzoyl)-oxymethyl]-pyridine methyliodide.

In human therapy the new compounds of the invention may be administered preferably orally or intravenously. The daily doses are about 1 to 10 mg/kg, preferably 4 to 8 mg/kg, a single oral or intravenous dose may be between 1.5 and 4 mg/kg, depending on the seriousness of the case to be treated.

The new antiarrhythmic agents of the invention are converted into pharmaceutical compositions by mixing the active compounds with the usual solid or liquid, inert, non-toxic pharmaceutical carriers and/or auxiliary materials. E.g. water, gelatine, lactose, starch, talc, magnesium stearate, vaseline, arabic gum, vegatable oils, polyalkylene glycol and the like may be used as carrier materials. The pharmaceutical compositions can contain other auxiliary materials, as preservatives, stabilizers, wetting or emulsifying agents, buffers, flavoring agents and the like.

The preparation of the new compounds of the invention is described in greater detail by the following examples; it is to be remarked, however, that the invention is by no means limited to the contents of these examples.

EXAMPLE 1

(a) 3-[(4-Fluorobenzoyl)-oxymethyl]-pyridine hydrochloride (2214)

10.5 g. of 3-hydroxymethyl-pyridine are dissolved in 60 ml. of anhydrous benzene. The solution is stirred at 20° C. and 7.6 g. of 4-fluorobenzoic acid chloride dissolved in 60 ml. of benzene are added dropwise thereto. The reaction mixture is refluxed for 30 minutes and then cooled to 20° C. The precipitated 3-hydroxymethyl-pyridine hydrochloride is filtered off. The filtrate is extracted with 250 ml. of 5% aqueous hydrochloric acid. The separated aqueous acidic layer is washed with 50 ml. of diethyl ether and then adjusted to pH=9 with 20% aqueous sodium carbonate solution. The basified solution is extracted three times with 50 ml. each of diethyl ether, the combined ether extracts are dried with anhydrous sodium sulfate, filtered and the filtrate is evaporated. The evaporation residue is dissolved in 80 ml. of a 1:1 mixture of isopropanol and ether and etheric hydrogen chloride solution is added to adjust the pH-value to 2. The precipitated acid addition salt is separated by filtration and recrystallized from a mixture of equal values of acetone and ethanol. 8.5 g. of 3-[(4-fluorobenzoyl)-oxymethyl]-pyridine (67.7% of theoretical yield) are obtained; m.p.: 142°–143° C.

The following compounds are prepared similarly, from the corresponding starting materials:
3-[(2-methylbenzoyl)-oxymethyl]-pyridine hydrochloride, m.p.: 152°–153° C. (2212)
3-[(3-methoxybenzoyl)-oxymethyl]-pyridine hydrochloride, m.p.: 137°–138° C. (2213)
3-[(3-methylbenzoyl)-oxymethyl]-pyridine hydrochloride, m.p.: 154°–155° C. (-)
4-[(3-methoxybenzoyl)-oxymethyl]-pyridine hydrochloride, m.p.: 181°–183° C. (2210)
4-[(2-methoxybenzoyl)-oxymethyl]-pyridine hydrochloride, m.p.: 188°–190° C. (2211)
4-[(4-methoxybenzoyl)-oxymethyl]-pyridine hydrochloride, m.p.: 186°–188° C. (2208)

4-[(4-fluorobenzoyl)-oxymethyl]-pyridine hydrochloride, m.p.: 199°-200° C. (2209)
4-(xanthene-9-carbonyloxymethyl)-pyridine hydrochloride, m.p.: 171°-172° C. (2204).

(b) 3-[(4-Fluorobenzoyl)-oxymethyl]-pyridine methyliodide (2217)

4.4 g. of 3-[(4-fluorobenzoyl)-oxymethyl]-pyridine hydrochloride prepared according to Example 1 (a) are dissolved in 40 ml. of acetone and 3 g. of methyl iodide are added thereto. The reaction mixture is refluxed for 30 minutes and then cooled to 0° C. The precipitated quaternary salt is separated by filtration and recrystalized from 100 ml. of anhydrous ethanol. 4.2 g. of 3-[(4-fluorobenzoyl)-oxymethyl]-pyridine methyliodide (60% of theoretical yield) are obtained; m.p.: 132°-133° C.

The following analogous quaternary salts are prepared similarly, from the corresponding hydrochlorides:
3-[(4-methoxybenzoyl)-oxymethyl]-pyridine methyliodide, m.p.: 172°-173° C. (2215)
3-[(3-methylbenzoyl)-oxymethyl]-pyridine methyliodide, m.p.: 162°-163° C. (-)
3-[(3-trifluoromethylbenzoyl)-oxymethyl]-pyridine methyliodide, m.p. 138°-139° C. (2216)
2-(xanthene-9-carbonyloxymethyl)-pyridine methyliodide, m.p.: 157°-159° C. (2207)
3-(xanthene-9-carbonyloxymethyl)-pyridine methyliodide, m.p.: 150°-151° C. (2206)
3-(xanthene-9-carbonyloxymethyl)-pyridine ethyliodide, m.p.: 141°-142° C. (2224)
4-(xanthene-9-carbonyloxymethyl)-pyridine methyliodide, m.p.: 188°-189° C. (2205).

EXAMPLE 2

2-[2-Chlorobenzoyl)-oxymethyl]-pyridine methyliodide (2221)

A mixture of 2.7 g. of 2-hydroxymethyl-pyridine and 8 g. of 2-chlorobenzoic acid methyl ester is heated to 60° C. and 1 ml. of 10% sodium methoxide solution is added thereto. The reaction mixture is heated for one hour at 100° C.; during this time the methanol formed in the reaction is distilled off. The reaction mixture is then cooled to 20° C., dissolved in 50 ml. of benzene and the solution is extracted with 25 ml. of 10% aqueous hydrochloric acid. The aqueous acid extract is treated with 3 g. of charcoal and then solid sodium hydroxide is added to reach a pH-value of 10. The basic solution is three times extracted with 30 ml. each of diethyl ether. The separated etheric layers are combined, dried over anhydrous sodium sulfate. filtered and the ether is distilled off from the filtrate. The obtained 2-[(2-chlorobenzoyl)-oxymethyl]-pyridine is converted into the quaternary methyliodide as described in Example 1 (b). 3 g. of 2-[(2-chlorobenzoyl)-oxymethyl]-pyridine methyliodide (32.5% of theoretical yield) are obtained; m.p.: 153°-155° C.

The following analogous quaternary salts are prepared similarly from the corresponding starting compounds:
2-[(2-methoxybenzoyl)-oxymethyl]-pyridine methyliodide, m.p.: 152°-153° C. (2218)
2-[(3-methoxybenzoyl)-oxymethyl]-pyridine methyliodide, m.p.: 162°-163° C. (2219)
2-[(4-methoxybenzoyl)-oxymethyl]-pyridine methyliodide, m.p.: 180°-181° C. (2220)
2-[(4-fluorobenzoyl)-oxymethyl]-pyridine methyliodide, m.p.: 178°-180° C. (2222).

What is claimed is:
1. An antiarrhythmic pharmaceutically effective compound selected from the group which consists of:
3-[(3-trifluoromethylbenzoyl)-oxymethyl]-pyridine methyliodide;
3-[(4-fluorobenzoyl)-oxymethyl]-pyridine methyliodide; and
2-[(2-chlorobenzoyl)-oxymethyl]-pyridine methyliodide.

2. 3-[(3-trifluoromethylbenzoyl)-oxymethyl]-pyridine methyliodide.

3. 3-[(4-fluorobenzoyl)-oxymethyl]-pyridine methyliodide.

4. 2-[(2-chlorobenzoyl)-oxymethyl]-pyridine methyliodide.

* * * * *